(12) United States Patent
Scarberry et al.

(10) Patent No.: US 7,568,483 B2
(45) Date of Patent: *Aug. 4, 2009

(54) PATIENT INTERFACE WITH RESPIRATORY GAS MEASUREMENT COMPONENT

(75) Inventors: Eugene N. Scarberry, Trafford, PA (US); Michael B. Jaffe, Cheshire, CT (US); Peter Chi Fai Ho, Pittsburgh, PA (US)

(73) Assignee: Ric Investments, LLC, Wilmington, DE (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/416,899

(22) Filed: May 3, 2006

(65) Prior Publication Data

US 2006/0249160 A1    Nov. 9, 2006

Related U.S. Application Data

(60) Provisional application No. 60/678,263, filed on May 6, 2005.

(51) Int. Cl.
*A62B 18/02* (2006.01)
*F16K 31/02* (2006.01)

(52) U.S. Cl. .............................. 128/206.21; 128/206.28; 128/204.23; 128/205.25

(58) Field of Classification Search ................. 128/857, 128/863, 20.24, 202.27, 206.12–207.13, 128/201.24
See application file for complete search history.

(56) References Cited

U.S. PATENT DOCUMENTS

| 4,177,381 A | 12/1979 | McClatchie et al. |
| 4,692,621 A | 9/1987 | Passaro et al. |
| 4,859,858 A | 8/1989 | Knodle et al. |
| 4,859,859 A * | 8/1989 | Knodle et al. ........... 250/504 R |
| 4,914,720 A | 4/1990 | Knodle et al. |
| 4,971,051 A | 11/1990 | Toffolon |
| 5,243,971 A | 9/1993 | Sullivan et al. |
| 5,282,473 A | 2/1994 | Braig et al. |
| 5,540,223 A | 7/1996 | Starr et al. |
| 5,616,923 A | 4/1997 | Rich et al. |
| 5,647,355 A * | 7/1997 | Starr et al. ............. 128/205.24 |
| 5,647,357 A | 7/1997 | Barnett et al. |
| 5,932,877 A | 8/1999 | Braig et al. |
| 6,192,886 B1 * | 2/2001 | Rudolph ................. 128/207.13 |

(Continued)

FOREIGN PATENT DOCUMENTS

WO    WO 03/022329 A2    3/2003

*Primary Examiner*—Justine R Yu
*Assistant Examiner*—Annette F Dixon
(74) *Attorney, Agent, or Firm*—Michael W. Haas

(57) ABSTRACT

A patient interface assembly for use with gas monitoring. The patient interface includes a mask shell having a portion that seals against the face of a patient and a mask attachment coupled to an opening of the shell. The mask attachment has a mask connection section coupled to the opening of the shell, an airway adapter section that serves as a gas measurement site for use in measuring a respiratory variable, and a breathing system connection section adapted to be coupled to a to a patient circuit. The gas measurement site, which includes a window, may be disposed on the conduit, the shell, or both. An access port, defined in the mask, the mask attachment, or both permits a sampling tube to be placed in fluid communication with an airway of a patient.

13 Claims, 13 Drawing Sheets

U.S. PATENT DOCUMENTS

| | | |
|---|---|---|
| 6,199,550 B1 * | 3/2001 | Wiesmann et al. ..... 128/204.23 |
| 6,397,847 B1 | 6/2002 | Scarberry et al. |
| 6,402,697 B1 | 6/2002 | Calkins et al. |
| 6,467,483 B1 | 10/2002 | Kopacko et al. |
| 6,606,993 B1 * | 8/2003 | Wiesmann et al. ..... 128/204.23 |
| 6,851,425 B2 | 2/2005 | Paul et al. |
| 7,004,163 B2 * | 2/2006 | Nashed .................. 128/201.22 |
| 7,004,168 B2 * | 2/2006 | Mace et al. ............ 128/206.21 |
| 2002/0174866 A1 | 11/2002 | Orr et al. |

* cited by examiner

PATIENT INTERFACE WITH RESPIRATORY GAS MEASUREMENT COMPONENT

CROSS-REFERENCE TO RELATED APPLICATIONS

This application claims priority under 35 U.S.C. § 119(e) from provisional U.S. patent application No. 60/678,263 filed May 6, 2005, the contents of which are incorporated herein by reference.

BACKGROUND OF THE INVENTION

1. Field of the Invention

The present invention relates to a respiration monitoring apparatus, and, more particularly, to a mask with a respiratory gas measurement site that obviates the need for the operator to separately assemble a respiratory gas measurement component to a mask and minimizes dead space and breathing circuit resistance.

2. Description of the Related Art

A variety of respiratory masks are known that have flexible seals and cover the nose, mouth, or both of a human patient. The mask seal, which is also commonly referred to as the cushion, creates a seal against the patient's face. Because of the sealing effect that is created, gases can be provided at a positive pressure within the mask for delivery to the airway of the patient.

The uses for such masks range from high altitude breathing, i.e., aviation applications, to mining and fire fighting applications, to various medical diagnostic and therapeutic applications. For example, such masks are used in the delivery of non-invasive positive pressure ventilation (NPPV) and the delivery of anesthesia. NPPV may be delivered as a continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure. NPPV also includes delivering life-supporting ventilation or ventilation that augments the patient's own respiratory effort.

Examples of conventional respiratory masks used in the medical field for providing a positive airway pressure to an airway of a patient are described in U.S. Pat. No. 5,243,971 to Sullivan et al., which teaches a bubble-type of patient interface in which the seal is attached to a shell and extends from the shell in a concave fashion. Other conventional masks are disclosed, for example, in U.S. Pat. No. 5,540,223 to Starr et al. and U.S. Pat. No. 6,467,483 to Kopacko et al.

A still further type of mask is described in U.S. Pat. No. 5,647,357 to Barnett et al. and U.S. Pat. No. 6,397,847 to Scarberry et al., which uses a gel material as the seal or cushion to maximize patient comfort and sealing properties. U.S. Pat. No. 4,971,051 to Toffolon teaches a mask in which the seal includes multiple flaps, again to optimize patient comfort and the sealing property.

The need to effectively titrate therapies, such as NPPV, based on clinical measures, such as the patient's arterial levels of carbon dioxide ($PaCO_2$) and/or changes in those levels, are being increasingly recognized. Recent studies have shown that in patients with dead space to tidal volume ratios less than 0.65, $PaCO_2$ and $PetCO_2$ are highly correlated. Additionally, it has been shown that changes in end-tidal carbon dioxide levels correlate well with changes in $PaCO_2$. It is changes in these levels that can be used to assess the effectiveness of changes in therapy.

The end-tidal carbon dioxide levels are determined from the patient's expiratory carbon dioxide gas. The patient's expiratory carbon dioxide gas is measured by gas analyzers that are typically categorized into two different types: (1) "non-diverting" or "mainstream" gas sampling systems; and (2) "diverting" or "sidestream" gas sampling systems. A mainstream gas sampling system includes a sample cell that is disposed along the main path of a breathing circuit through which a patient's respiratory gases flow. As a result, all of the patient's inspired and expired respiratory gases pass through the sample cell, which is also known as a "cuvette". A gas sensing system, which includes the elements necessary for monitoring respiratory gases, is coupled to the sample cell to measure the constituents of gas passing through the sample cell. For infrared gas sensing, the gas sensing system includes a radiation source and detector. An example of such a conventional mainstream gas measurement system using infrared gas sensing is described in U.S. Pat. No. 4,914,720 to Knodle et al.

A sidestream gas sampling system transports a portion of sampled gases from the sampling site, which is typically a breathing circuit coupled to the patient's airway or directly at the patient's airway, through a sampling tube to the sample cell, where the constituents of the gas are measured by a gas sensing system. Gases are continuously aspirated from the sample site through the sampling tube and into the sample cell, which is located within a gas measurement instrument. Examples of conventional sidestream gas sampling systems are taught in U.S. Pat. No. 4,692,621 to Passaro et al.; U.S. Pat. No. 4,177,381 to McClatchie; U.S. Pat. No. 5,282,473 to Braig et al.; and U.S. Pat. No. 5,932,877 also issued to Braig et al.

The increasing sophistication of therapies, such as NPPV and the currently available gas monitoring technologies, make the combination of these two modalities attractive and potentially clinically beneficial for the management of patients suffering from respiratory failure. Their actual use in clinical practice is limited due to a number of factors that are methodological, technical, and educational in nature. Methodological problems relate to the selection of the proper patient interface, management of leaks around the mask seals, which complicates the interpretation of the measurement as well as adding to inconvenience and the added complexity of the gas measuring apparatus. Technical problems of combining gas measurement technologies and masks relate to the added deadspace of the additional breathing circuit components, such as the airway adapter portion and its associated rebreathing, the added pressure drop of the additional breathing circuit component and its affect on the therapy being delivered, and the need to provide for the possible use of either sidestream or mainstream gas sampling technologies. For example, the choice of a nasal, full face, or a mask covering nose, mouth, and eyes, in combination with other factors, determines the appropriate gas sampling method to use for $CO_2$ measurement. The success of respiratory gas monitoring with therapies, such as NPPV, depends on understanding and controlling these factors.

Given these problems associated with monitoring respiratory gases from patients with masks, it is desirable to provide a mask with both mainstream and sidestream respiratory gas monitoring capabilities. Such a mask would be beneficial if it also minimized the added dead space and the pressure drop associated with the application of conventional gas monitoring approaches. Additionally, such a mask is beneficial if it also permits the effectiveness of therapies, such as NPPV, to be assessed and provides convenience and simplicity to the user, thereby encouraging greater use of such therapies.

SUMMARY OF THE INVENTION

Accordingly, it is an object of the present invention to provide a patient interface assembly for use with gas monitoring that overcomes the shortcomings of conventional gas monitoring approaches. This object is achieved according to one embodiment of the present invention by providing a patient interface assembly that includes a shell having a first opening and a second opening and a seal. The seal includes a first end portion coupled to the second opening of the shell, and a second end portion for sealing engagement with a face of a patient. The patient interface assembly also includes a mask attachment coupled to the first opening of the shell. The mask attachment has a mask connection section coupled to the opening of the shell, an airway adapter section for use in measuring a respiratory variable, and a breathing system connection section adapted to be coupled to a to a patient circuit.

It is a still further object of the present invention to provide a patient interface assembly that includes a shell, a seal coupled to the shell, a conduit coupled to the shell, and a gas measurement site disposed on the conduit, the shell, or both, wherein the gas measuring site includes a window.

Yet another object of the present invention is to provide a respiratory gas analysis system that includes a mask having an opening and a mask attachment operably coupled to the opening in the mask. An access port is defined in the mask, the mask attachment, or both. A sampling tube is in fluid communication with an airway of a patient through the access port. A transducer is secured to the sampling tube, and a processor communicates with the transducer. The processor calculates at least one respiratory parameter using the signal from the transducer.

It is a further object to provide a method of sidestream respiratory gas analysis that includes applying a mask assembly to a patient; placing a sampling tube in fluid communication with an airway of a patient; communicating a flow of gas from the patient via the sampling tube to a sidestream gas measurement assembly; and analyzing the at least one parameter using the sidestream gas measurement assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENT EMBODIMENTS

The particular embodiments described herein are intended in all respects to be illustrative rather than restrictive. Alternative embodiments will become apparent to those of ordinary skill in the art to which the present invention pertains without departing from its scope.

Figure 1:
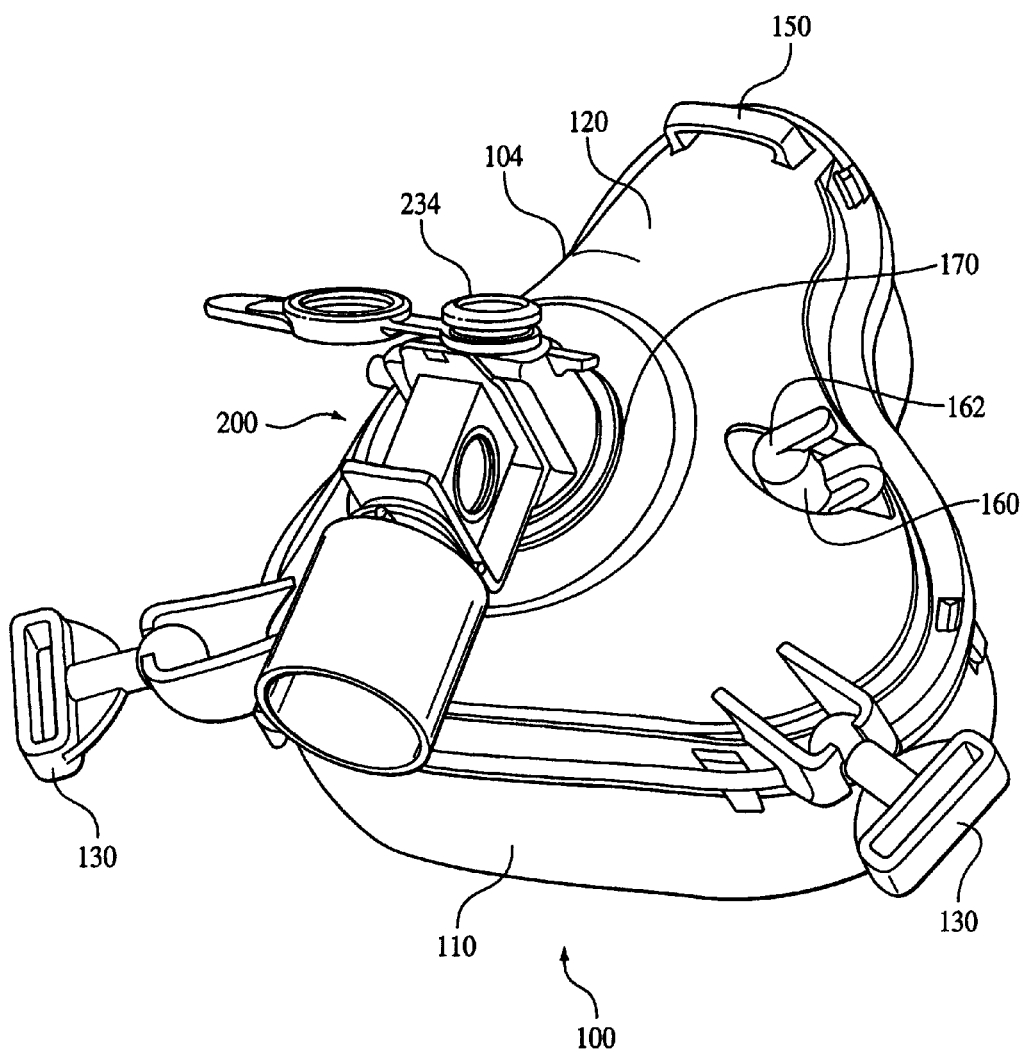
FIG. 1 is a perspective view of a first embodiment of a patient interface assembly according to the principles of the present invention.
Figure 2:
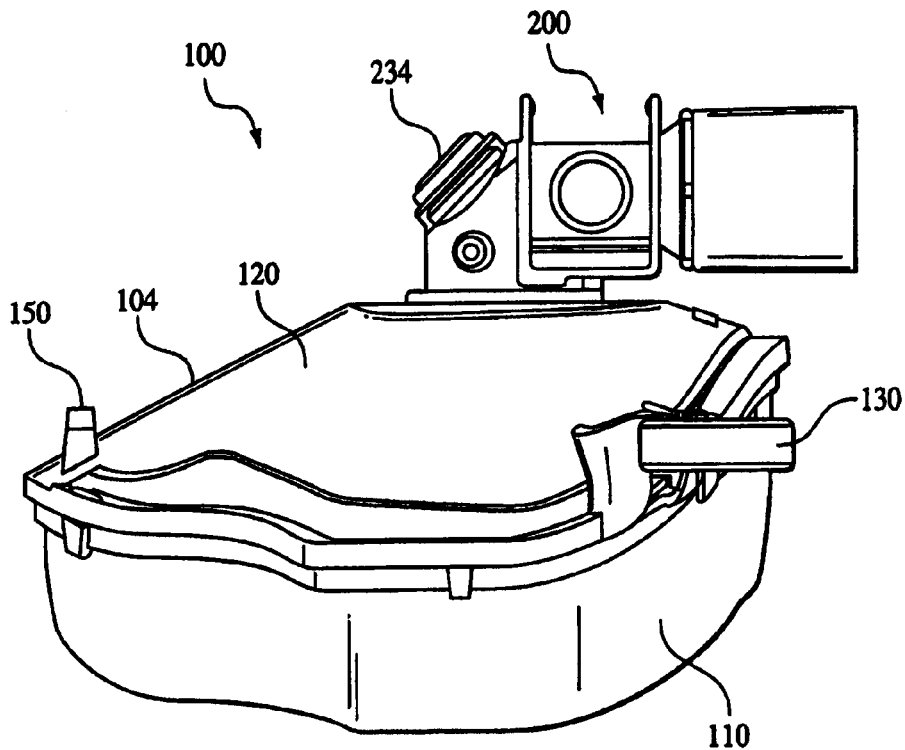
FIG. 2 is a side view of the patient interface assembly of FIG. 1.
Figure 3:
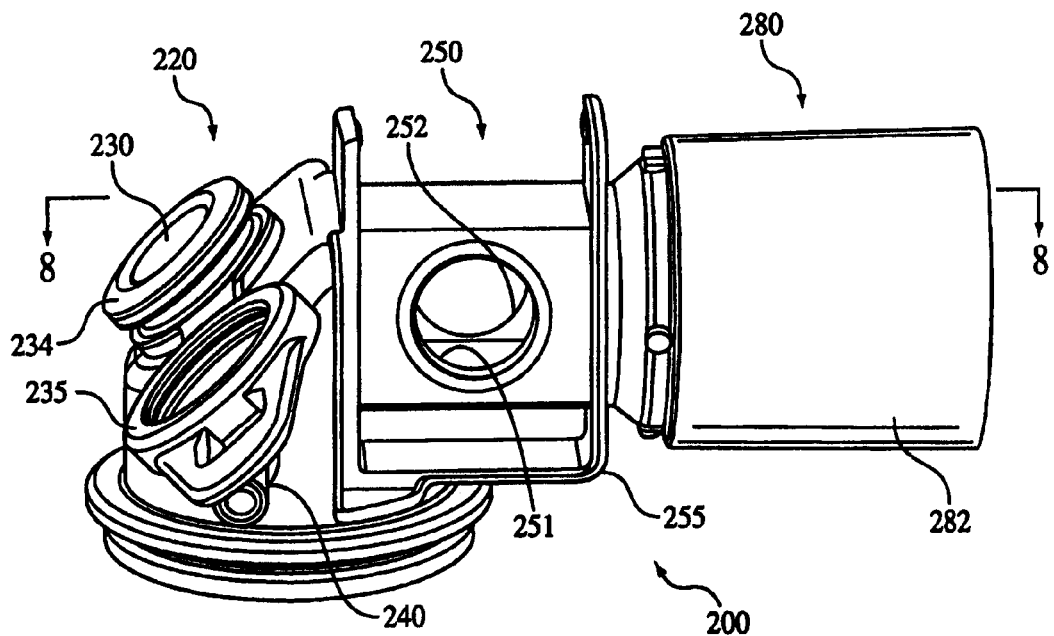
FIG. 3 is a side perspective view of the mask attachment in the patient interface assembly of FIG. 1.
Figure 4:
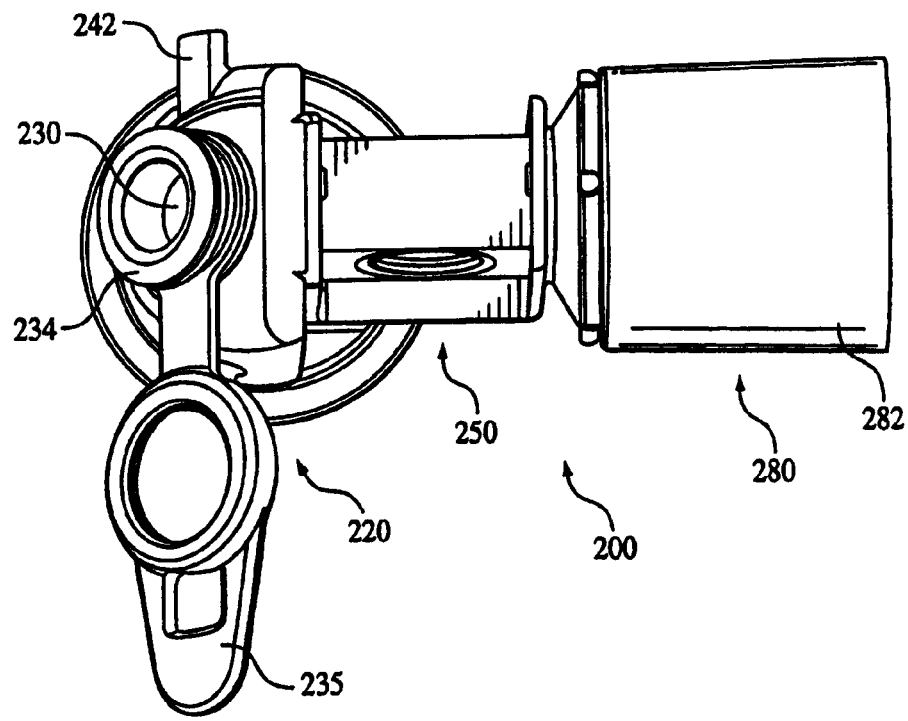
FIG. 4 is a top perspective view of the mask attachment in the patient interface assembly of FIG. 1.
Figure 5:
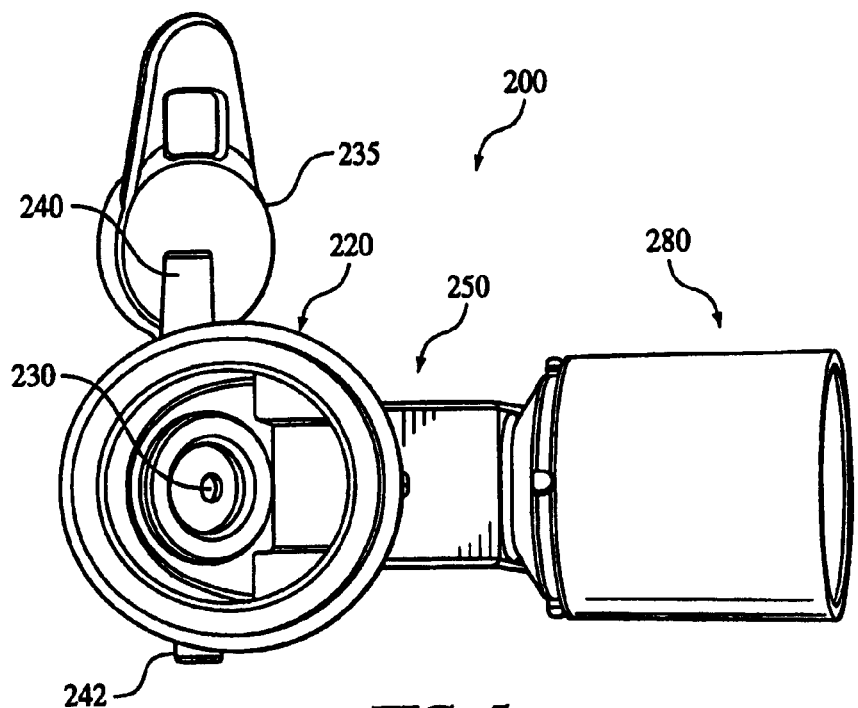
FIG. 5 is a bottom perspective view of the mask attachment in the patient interface assembly of FIG. 1.
Figure 6:
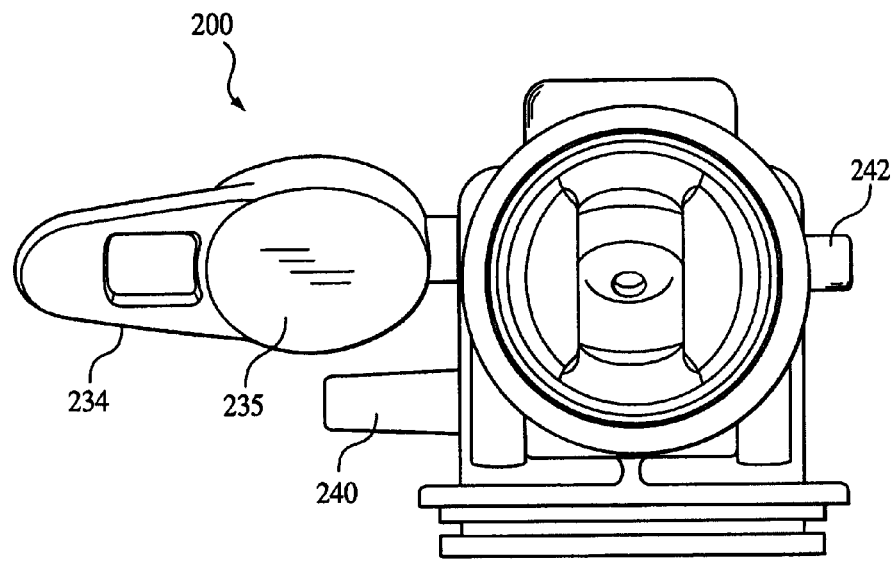
FIG. 6 is a end perspective view of the mask attachment in the patient interface assembly of FIG. 1.

FIGS. 1 and 2 illustrate a first exemplary embodiment of a patient interface assembly 100 according to the principles of the present invention. Patient interface assembly 100 includes a mask 104 and mask attachment 200. Mask 104 includes a mask shell 120 or body portion and a seal 110. The mask shown is a full facemask that covers the user's nose and mouth. It is to be understood, however, that the present invention contemplates that mask 104 is any mask suitable for providing a sealed interface with an airway of a patient. Examples of such masks include a nasal mask that covers only the user's nostrils, a total facemask, or helmet that covers a major portion of the user's face or head.

Mask attachment 200 provides an "L" shaped conduit or 90° elbow coupled to the mask shell. In an exemplary embodiment, the mask attachment is rotateably coupled to the mask shell. It is to be understood that the invention contemplates other configurations, shapes, and angles for the mask attachment, such as straight (180°) and 45° angle.

As noted above, mask 104 includes a shell or body portion 120 to which seal 110 is affixed. Shell 120 also defines an opening 170, or other suitable means, for connecting mask 104 to mask attachment 200 and to a supply of gas (not shown) for administration to a patient. Shell 120 further includes two outwardly projecting strap retaining tabs 130 and an upwardly projecting strap retaining tab 150, each having suitable elongated apertures that receive and retain suitable conventional head straps (not shown) for retaining the patient interface assembly to the face of a patient. An optional pressure port 160 with a cap 162 for sealing the port is shown. Port 160 may be used for pressure monitoring, for example, for providing feedback to a therapy delivery system. Port 160 can also be used for delivering a flow of gas, such as oxygen, to the user. It is to be further understood that the shell and seal member can be any conventional shell and seal member known in the art.

Referring to FIGS. 3-9, the details of an exemplary first embodiment of mask attachment 200 will be described. Mask attachment 200 consists of a mask connection section 220, an airway adapter section 250, and a breathing system connection section 280. Mask connection section 220 provides a conduit for communicating gas between mask shell 120 and airway adapter section 250. Mask connection section 220 also couples the mask attachment to the mask shell. An optional resealable opening 232 serves as an access port (opening) for communicating with the interior of the mask and/or mask attachment.

Airway adapter section 250 provides a conduit for communicating gas between mask connection section 220 and breathing system connection section 280. A swivel connection 278 couples the airway adapter section to the breathing system connection section. Additionally apertures 251 and 252 provide optical access to the gas stream within this section. Breathing system connection section 280 provides a conduit for communicating gas between the airway adapter section and breathing circuit. Breathing system connection section 280 couples the patient interface assembly to a therapy device, such as a ventilator or pressure support system.

In the exemplary embodiment, the interior surfaces of the mask connection section 220 are tapered such that the flow between the mask connection section 220 and airway adapter section 250 remains relatively undisturbed. Similarly, during exhalation, this tapering permits a measurement that is more representative of the patient's expiratory gas and less diluted by gas mixing to be made. Additionally, tapering reduces the pressure drop of the mask attachment so that therapy, such as NPPV, can be administered more efficiently and with less resistance during the exhalation and inhalation phases.

In the exemplary embodiment of this invention, opening 232 is provided in mask connection section 220. A grommet 234, which contains an interior passage 230 and cap 235, is assembled to opening 232. Interior passage 230 serves as an access port so that a tubular structure, such as a catheter, can be placed within the mask and, if desired, placed into the nares or oral cavity of the user without breaking the seal between the mask and the users face and interrupting the current therapy. The present invention contemplates using the access port for other applications, such as, but not limited to, the placement of a gas sampling catheter, a suctioning catheter, a flexible bronchoscope, or a catheter for respiratory drug delivery in or near an airway of the user.

The mask attachment is preferably connected to the mask via a coupling 221 in such a manner to allow rotation between the mask shell and the mask attachment. This permits easier access of the caregiver to the patient's face that may otherwise be partially obstructed by the breathing tubing of the breathing circuit, as well as allows the access port to be positioned to permit more convenient placement of a catheter or bronchoscope. Port 232 also permits the positioning of a tubular structure close to the nares or oral cavity of the user, thereby enabling more efficient collection of the patients expiratory gas. The access port can include a plug with a cover or the plug can be made of an inexpensive material, which can be easily punctured and will reseal upon removal of the catheter, such as materials used in vascular access ports. Port 232 is dimensioned such that known gas sampling, suction, or delivery catheters and bronchoscopes can fit through the port leaving a sufficient clearance, e.g., greater than 6 mm diameter.

The central portion of airway adapter section 250 is generally parallelepiped with a flow passage 210 extending through the mask connection section, the airway adapter section, and the breathing circuit connection section. The mask connection section and breathing system connection section are preferably axially aligned with the airway adapter section. Airway adapter section 250 provides a seat for a securably removable transducer 50. (See FIG. 10) An integral, U-shaped casing element 255 positively locates a transducer housing 52 on the adapter section. Arrow 136 shows the direction in which the transducer housing is coupled to and uncoupled from airway adapter section 250. The transducer housing snaps into place on the airway adapter section. Examples showing the attachment of a transducer to airway adapters are disclosed in U.S. Pat. Nos. 4,859,858 and 4,859,859, the contents of which are incorporated by reference. The techniques for securing the transducer to the airway adapter taught by these patents are applicable to the attachment of the transducer to airway adapter section 250. In an exemplary embodiment, no tools are needed to assemble or remove the transducer housing from the airway adapter section.

One suitable $CO_2$ gas sensor suitable for use as transducer 50 is the CAPNOSTAT® brand of infrared (IR) sensor offered by Respironics Novametrix of Wallingford, Conn. It can be appreciated to one of ordinary skill in the art that the purpose of the airway adapter section is to provide access to the flow of gas within the conduit, so that components of the gas may be measured. As such, any gas sensing device, whether it is securably removable, or affixed to, or integrated with the airway adapter section may be used.

Breathing system connection section 280 connects the airway adapter section with the tubing of the breathing circuit. Generally, the outer diameter of a cylindrical connector 282 of the breathing system connection section is sized and tapered to conform to existing breathing system circuit connector standards. The breathing system can be coupled to a single limb or dual limb breathing circuit. With a single limb breathing circuit, an exhalation valve is provided at or near the mask. With a dual limb breathing circuit, a 'Y' or 'T' piece with separate expiratory and inspiratory limbs is coupled to the breathing system connection section.

To facilitate the measurement of constituents of the gases in flow passage 210, infrared light radiation passes through an infrared-transparent portion of the airway adapter section. This infrared-transparent portion may be realized by means including, but not limited to, apertures with infrared transparent windows or molding the airway adapter portion of infrared transparent material. In the exemplary embodiment, apertures 251 and 252 are formed in airway adapter section 250. Apertures 251 and 252 are covered by first and second axially aligned windows 253 and 254, respectively. Windows 253 and 254 preferably have a high transmittance for radiation in at least the intermediate infrared portion of the electromagnetic spectrum. The substantial axial alignment of first window 253 and second window 254 allows an infrared radiation beam to travel from an infrared emitter in one leg of transducer housing 50 transversely through airway adapter section 250 and through the gases flowing through flow passage 210 to an infrared detector in the opposing, substantially parallel leg of transducer housing 52. With transducer housing 52 assembled to the airway adapter section, these apertures are aligned along an optical path 259. Thus, an infrared radiation beam can travel from the infrared radiation emitter unit in transducer housing 52 transversely through airway adapter section 250 and the gas or gases flowing through airway adapter flow passage 210 to an infrared radiation detector unit of transducer housing 52.

The internal configuration and design of an exemplary infrared detector, which preferably monitors, in real time, the amounts of respiratory gases, such as $CO_2$, and $N_2O$ or anesthetic agents in the respiration of an individual, is thoroughly discussed in U.S. Pat. No. 5,616,923 (hereinafter "the '923 patent"). It is understood that infrared $CO_2$ monitor devices, such as those disclosed in U.S. Pat. Nos. 4,859,858 and 4,859,859 and in the '923 patent, as well as other gas detection devices, are contemplated for use in transducer housing 50. The other gas detection devices suitable for use in the present invention include, but are not limited to, (a) devices that monitor gas using chemical based techniques, such as luminescence, (b) devices that monitor gas using electrochemical and physical methods, such as Raman spectroscopy, and (c) devices that monitor gas using nanotube based methods. In addition to one or more infrared sensors, the infrared detector of the present invention can include any combination of other components, including a reference sensor, optics (e.g., lenses, filters, mirrors, beam splitters, etc.), coolers, and the like. The infrared signals detected by infrared detector can be ratioed to provide a signal accurately and dynamically representing the amount of $CO_2$, $N_2O$ or an anesthetic agent flowing through airway adapter section 250.

Figure 7:
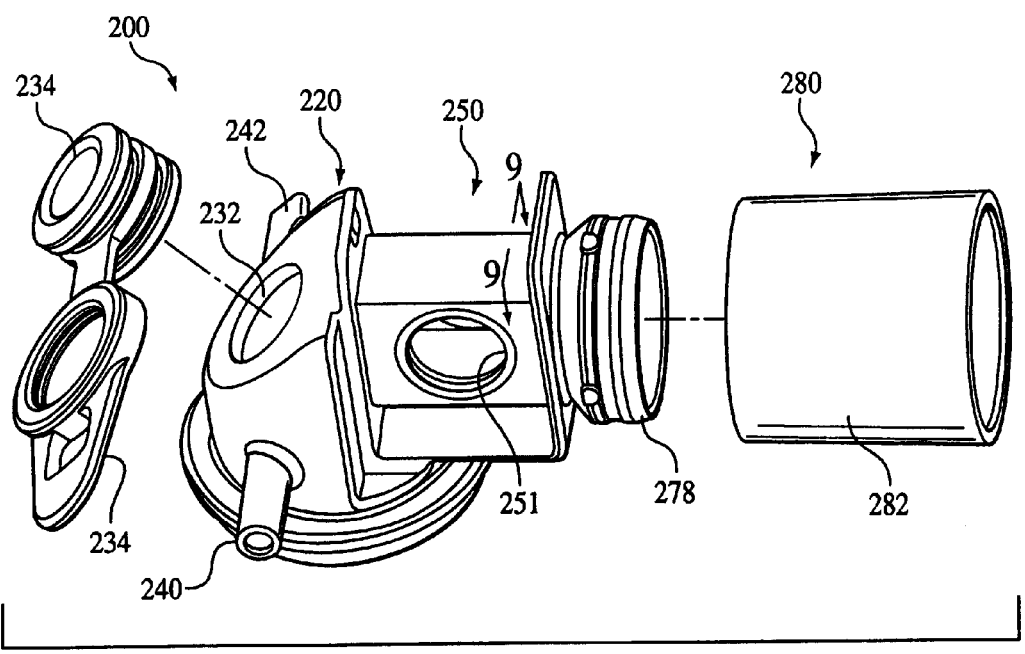
FIG. 7 is a exploded view of the mask attachment in the patient interface assembly of FIG. 1.

Referring to FIG. 7, an exploded perspective view of mask attachment 200 is shown, including mask connection section 220, airway adapter section 250, and breathing circuit connection section 280. Swivel connection 278 provides a rotateable coupling between breathing circuit connection section 280 and airway adapter section 250. The swivel fitting is provided on the patient end of the mask attachment and typically conforms to the requirements of a harmonized international standard but it is not limited to such fitting. The swivel fitting can be featured in various fittings including the ISO 22 Male or further integrated into the exhalation port of a disposable circuit with a non-standard fitting.

Figure 8:
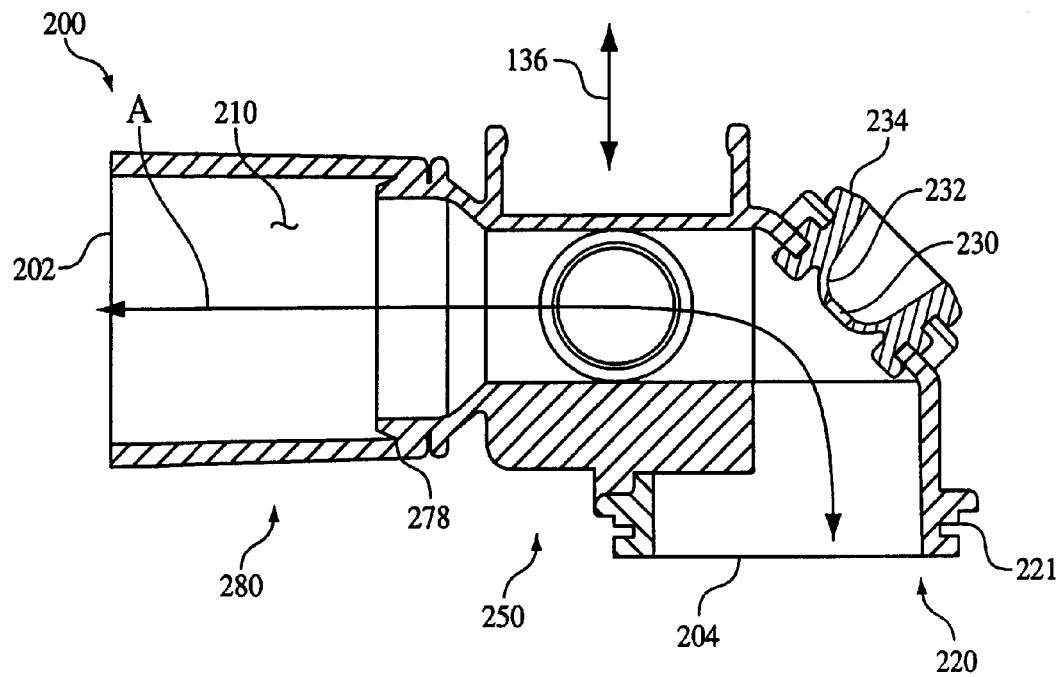
FIG. 8 is a cross-sectional view of the mask attachment taken along line 8-8 of FIG. 3.
Figure 9:
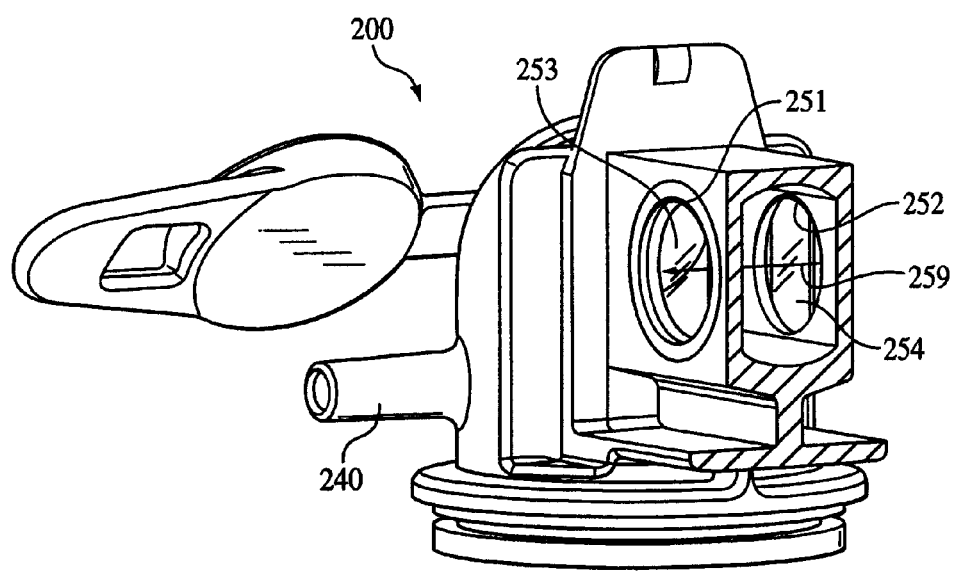
FIG. 9 is a cross-sectional perspective view of the mask attachment taken along line 9-9 of FIG. 7.

Referring to FIG. 8, the cross-section view of mask attachment 200 illustrates flow passage 210 through the mask attachment. The gas flow through the mask attachment is represented by arrow A. Gas flow during inspiration enters mask attachment end 202 and exits mask attachment end 204. During expiration, the gas exits the mask, enters the mask attachment via mask attachment end 204, and exits the mask attachment at mask attachment end 202.

Figure 10:
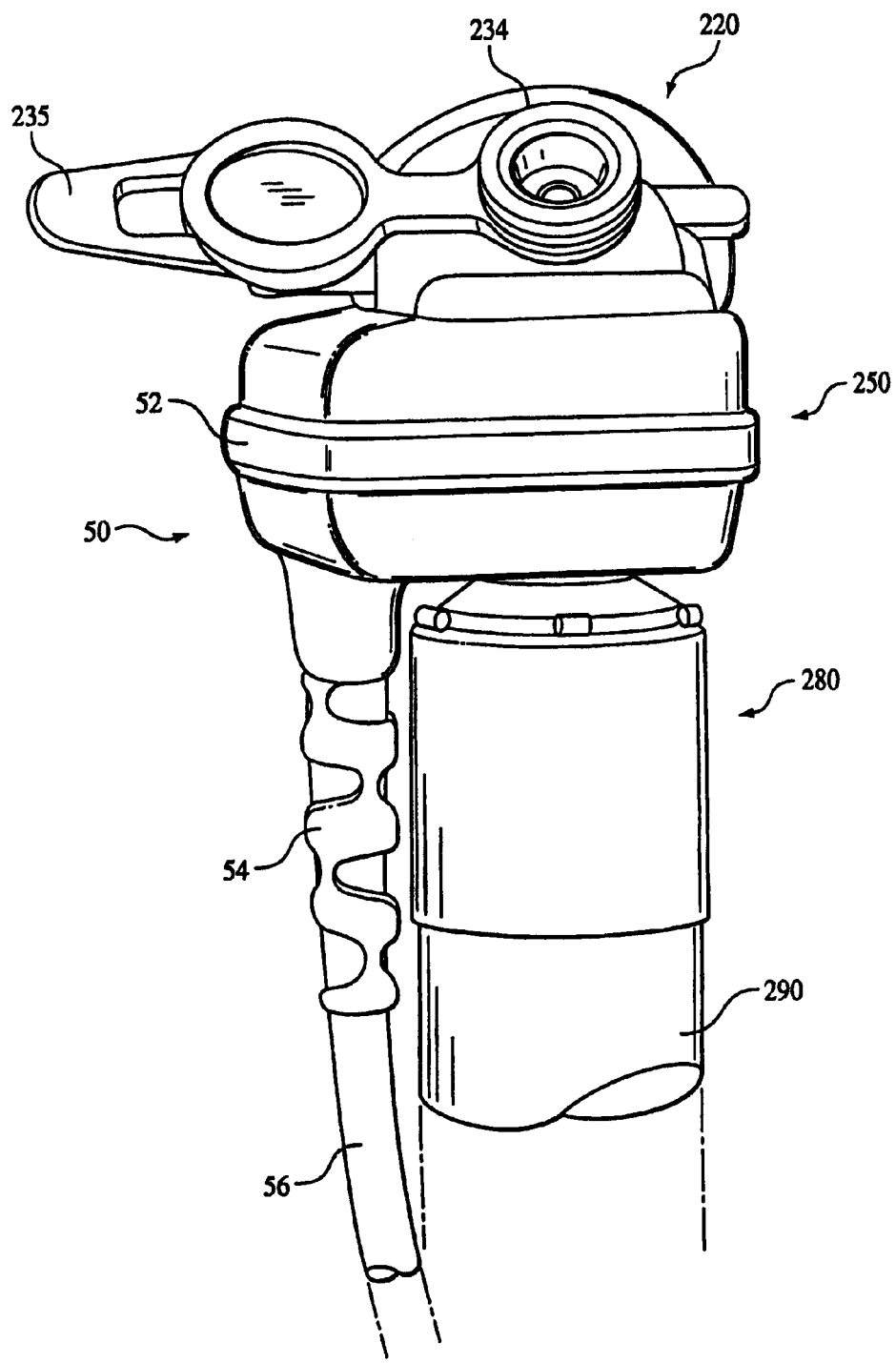
FIG. 10 is a top perspective view of the mask attachment showing a mainstream gas sensor transducer housing removably secured to the airway adapter portion of the mask attachment.

FIG. 10 shows a top perspective view of the mainstream gas measurement device transducer 50 removably secured to airway adapter section 250 and a breathing circuit tubing 290 attached to breathing system connection section 280. A strain relief element 54 and a cable 56, which communicates with the host monitoring system, are also shown. It can also be appreciated that it would be desirable to eliminate the cable and communicate data wirelessly to the host monitoring system. The present invention contemplates using any suitable wireless communication technique to communicate with the transducer. In an exemplary embodiment, a low-power sensor oriented protocols, such as IEEE 802.15.4 (Zigbee), may be used for this purpose.

Figure 11:
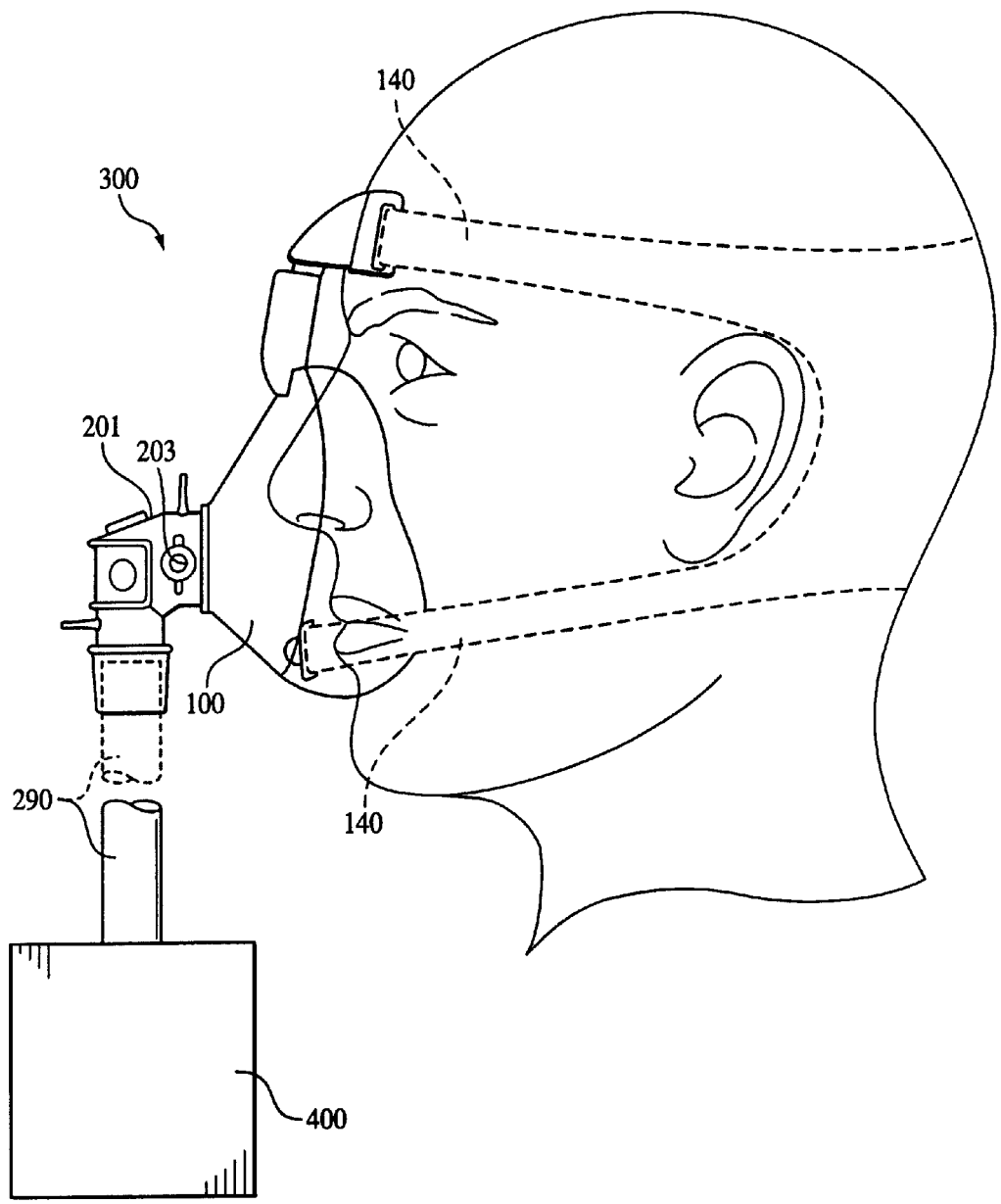
FIG. 11 is a side view of a second embodiment of a patient interface assembly according to the principles of the present invention shown positioned on a user's face.
Figure 12:
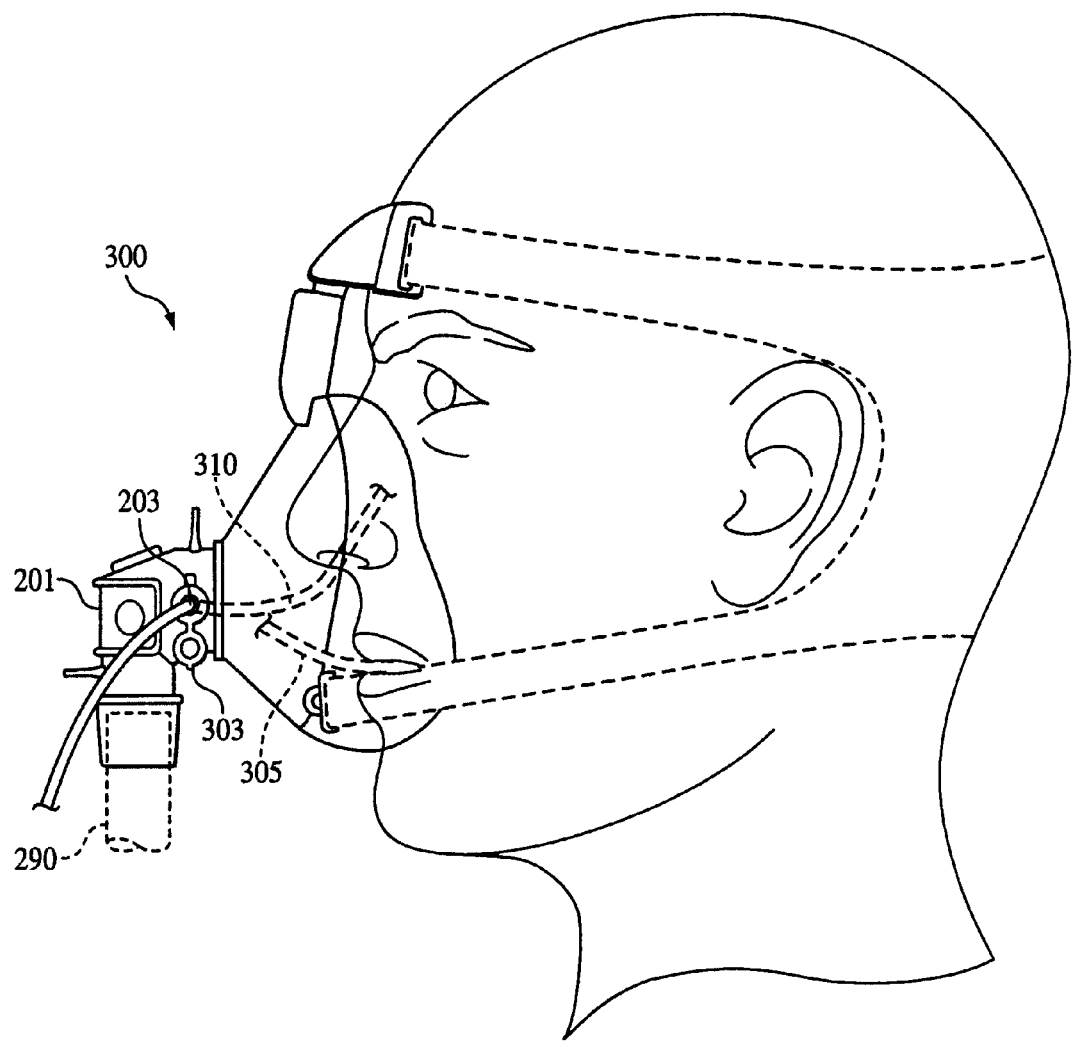
FIG. 12 is a side view of the patient interface assembly of FIG. 11 showing a catheter inserted in the nares or lips of the user.

FIGS. 11-12 illustrate a second embodiment of a patient interface assembly 300 including a mask attachment 201 according to the principles of the present invention and shown positioned on a user's face. A headgear 140 secures the patient interface assembly on the user. The present invention contemplates that the headgear can be any conventional headgear suitable for this purpose. Thus, the details of the headgear are omitted from the present description for the sake of brevity As shown in FIG. 11, mask attachment 201 is in fluid communication with breathing circuit tubing 290 and a respiratory device 400. The present invention contemplates that respiratory device 400 is any respiratory, ventilatory, pressure support, or other device used to communicate gas with an airway of a patient. Such devices include, but are not limited to ventilators, pressure support devices, humidifiers, nebulizers, or any combination thereof.

Mask attachment 201 is generally similar to mask attachment 200 except that in the embodiment shown in FIGS. 11 and 12, the mask attachment includes an access port 203 positioned laterally on the mask attachment, i.e., on a side of the mask connection section. The access port, which is covered by a grommet 303, facilitates the placement of a flexible catheter 310 in the nares or a flexible catheter 305 in the oral cavity of a user. This flexible catheter is used for collecting gas from a gas sampling site. Typical gas sampling sites include, but are not limited to, inside the mask, at or near the nares, and inside the nasal or oral cavities. The present invention also contemplates inserting a flexible bronchoscopy device into the patient using access port 203.

Figure 13:
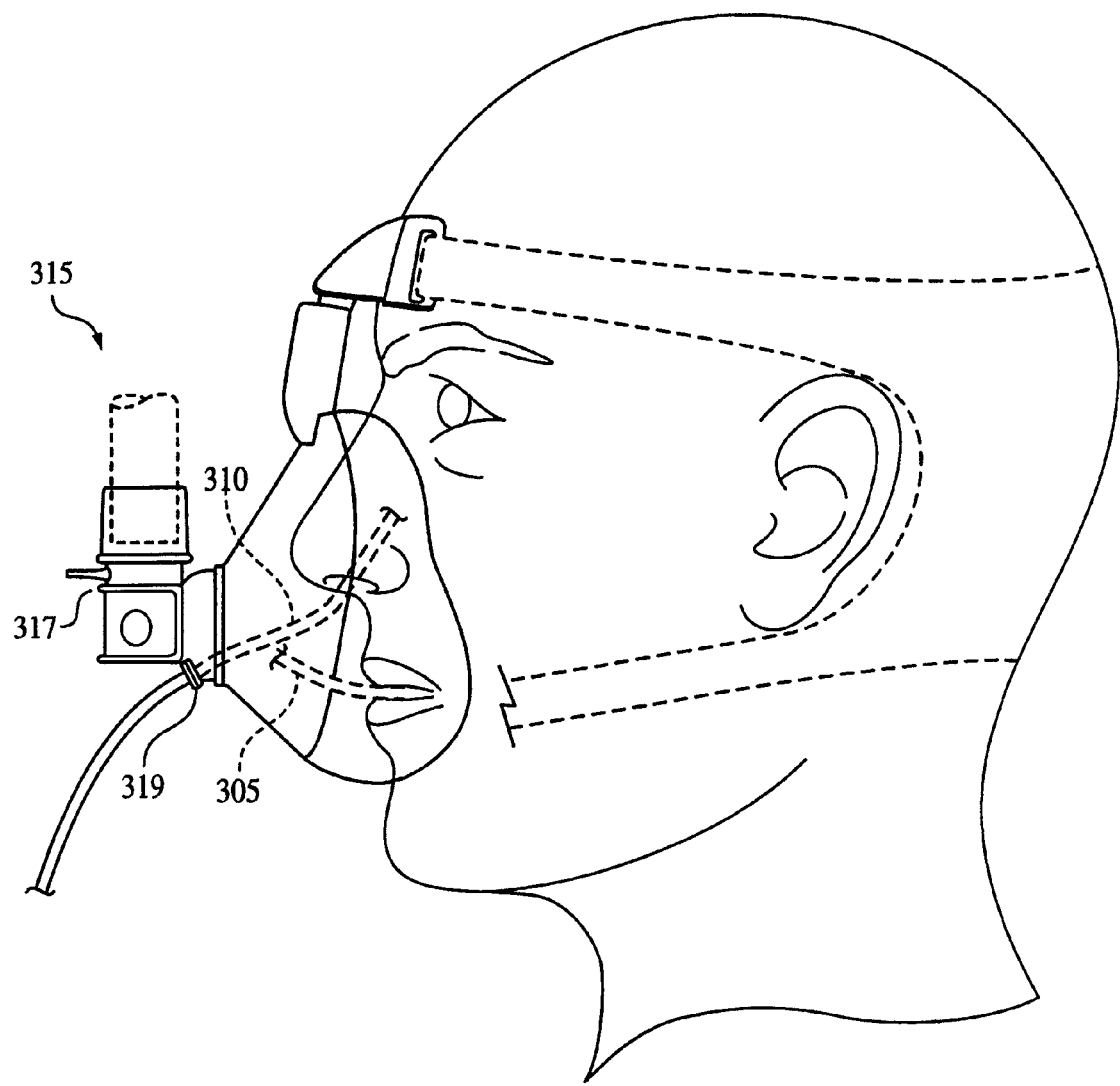
FIG. 13 is a side view of a third embodiment of a patient interface assembly according to the principles of the present invention shown positioned on a user's face with a catheter inserted in the nares or lips of the user.

FIG. 13 illustrates a third embodiment of a patient interface assembly 315 including a mask attachment 317 according to the principles of the present invention. Mask attachment 317 is generally similar to that of the previous embodiments, except for the location of the access port. In this embodiment, an access port 319 is provided at a location that is slightly offset from the gas flow path so to minimize any interference between that the catheter or other implement inserted into the port and the gas flow to and from the patient. In the illustrated embodiment, mask attachment 317 is shown oriented in an upward direction, which simplifies the placement of a flexible catheter for gas sampling or bronchoscopy in the nares or oral cavity of a user. It is to be understood that the structural features of mask attachment 317, including providing a grommet to cap the access port, correspond to features of mask attachment 200 shown in FIGS. 3-9.

Figure 14:
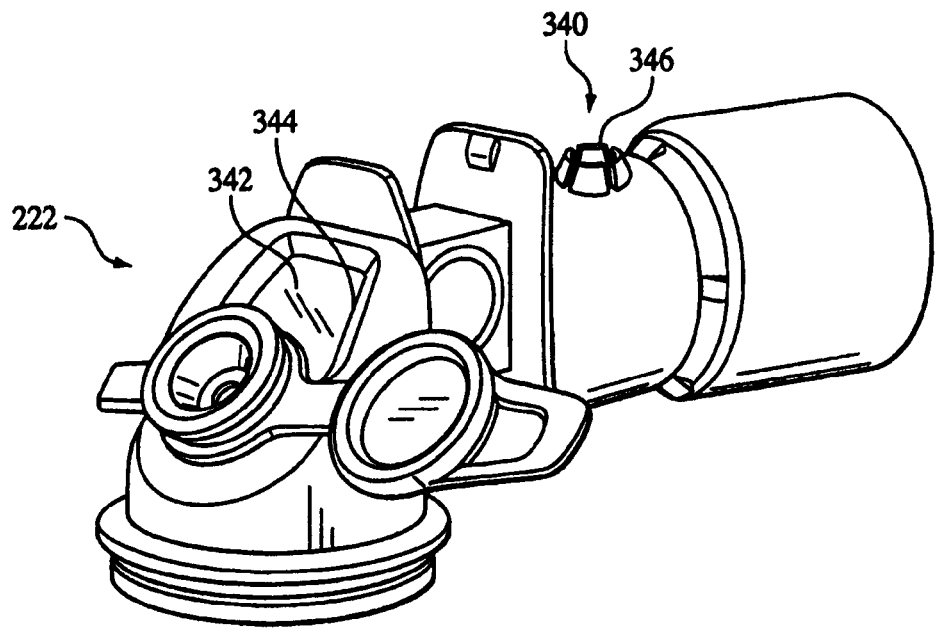
FIG. 14 is a side view of a fourth embodiment of mask attachment with an entrainment valve.

FIG. 14 illustrates a fourth embodiment of a mask attachment 340 in accordance with the principles of the present invention. Mask attachment 340 is generally similar to that of previous embodiments, except that the mask attachment includes an entrainment valve 222 positioned on the mask connection section. The entrainment valve serves as safety mechanism in single limb circuits. During normal use, i.e., when the pressure support system is providing a flow of gas to the breathing circuit, the positive pressure in the patient circuit urges a valve element 342 into a sealed position over an opening 344 provided in the mask attachment. If the pressure in the system drops below a desired level, for example, if the pressure support system ceases operating, valve element 342 moves to an open position in which opening 344 is unblocked to allow the user to breathe room air. Examples of entrainment valves suitable for use in the present invention are taught by U.S. Pat. Nos. 6,851,425 and 5,647,355, the contents of which are incorporated herein by reference. It is to be understood that the present invention contemplates using any suitable entrainment valve, and is not intended to be limited to those disclosed above or described in the references patents.

FIG. 14 also illustrates a "castle" exhaust port 346 that exhausts gas from the system to ambient atmosphere. This type of exhaust port provides a fixed orifice opening in the conduit so that gas, such as exhaled gas, can escape to the atmosphere. The "castle" configuration is provided to prevent the exhaust orifice from being blocked. It is to be understood that that present invention contemplates providing any conventional exhaust assembly on the mask attachments described herein or coupled to the mask attachments. Examples of exhaust assemblies suitable for use in the present invention are taught by U.S. Pat. No. 6,851,425, the contents of which are incorporated herein by reference.

Figure 15:
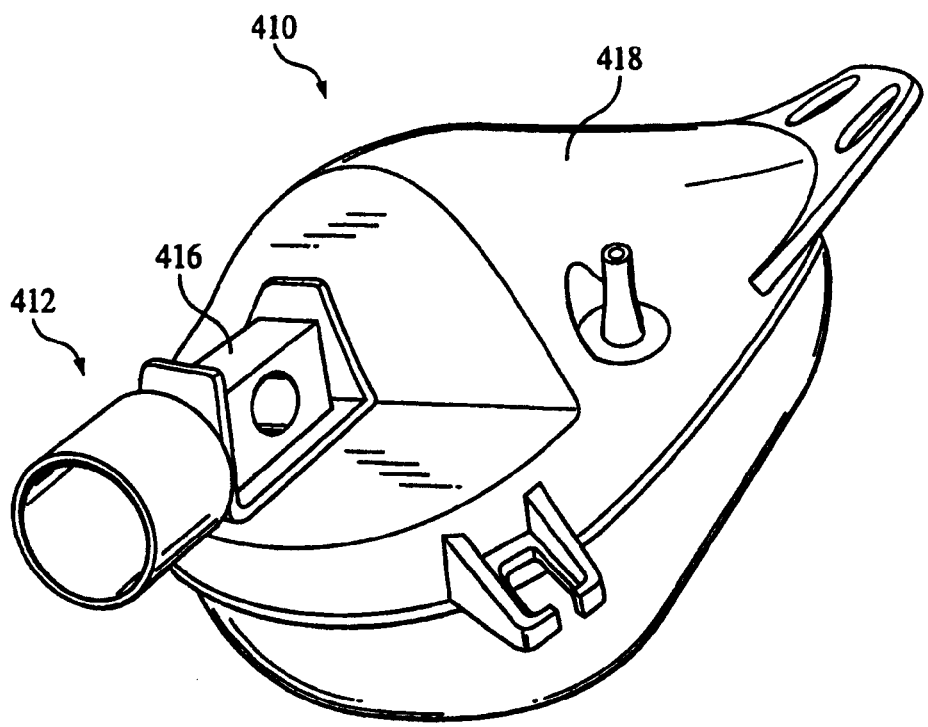
FIG. 15 is a perspective view of a fifth embodiment of a patient interface assembly that includes an integrated facemask and gas measurement site.
Figure 16:
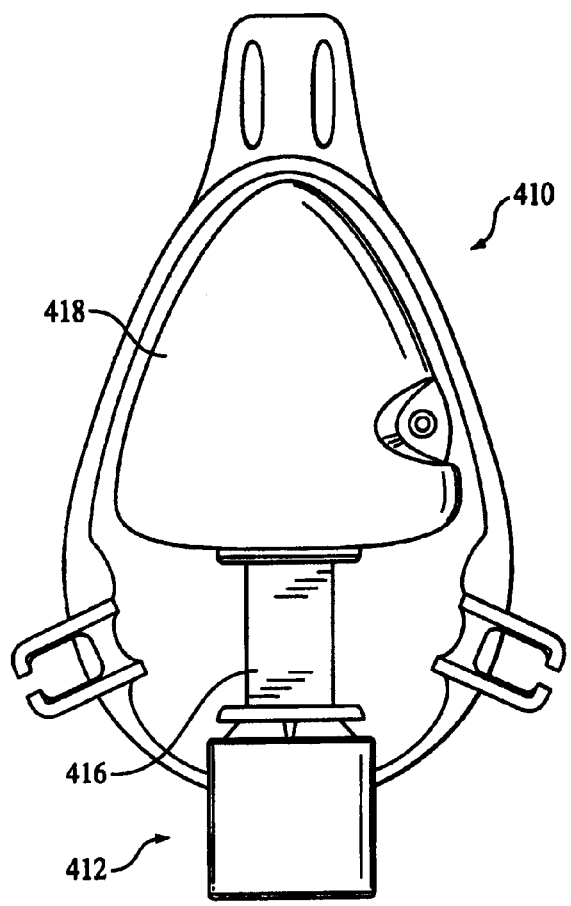
FIG. 16 is a top perspective view of the patient interface assembly of FIG. 15.
Figure 17:
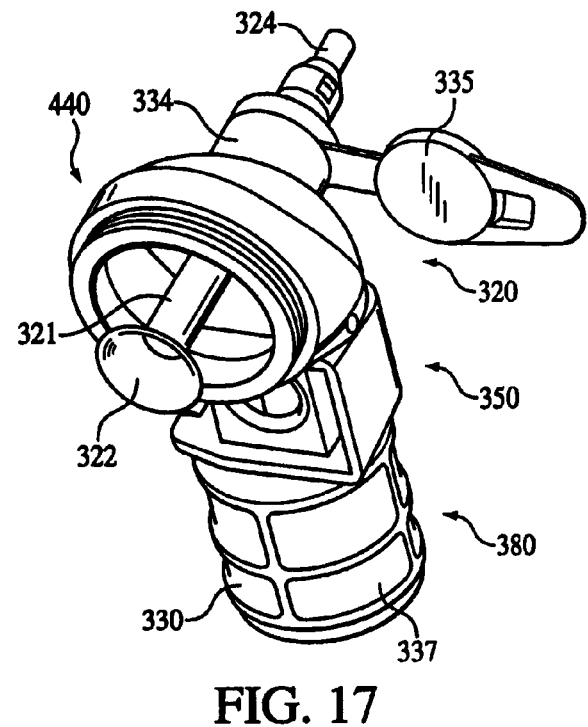
FIG. 17 is a perspective view of a sixth embodiment of mask attachment with an entrainment valve and gas collector according to the principles of the present invention.
Figure 19:
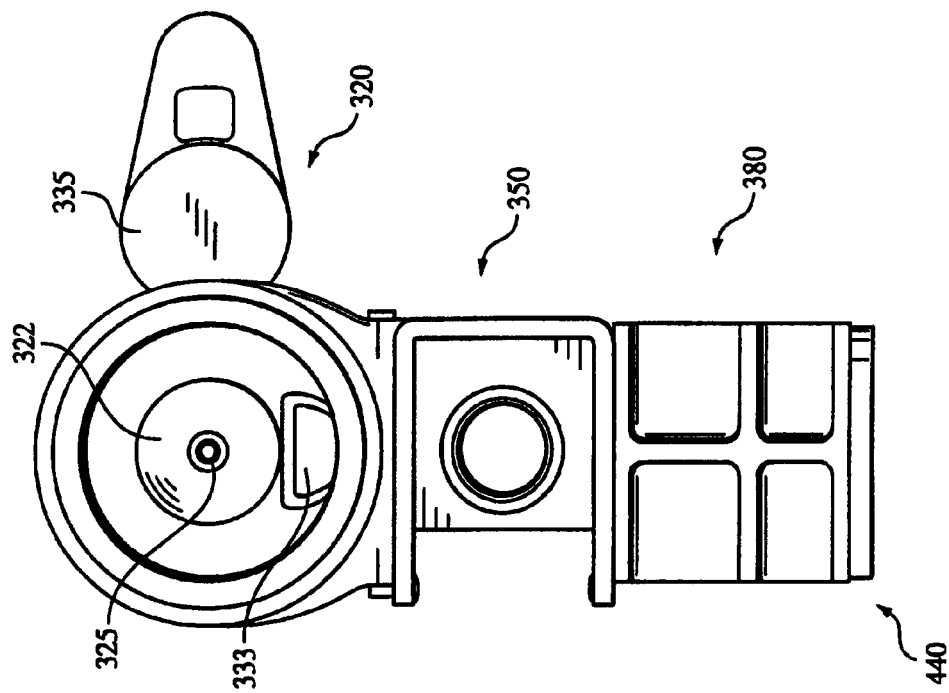
FIG. 19 is an end view the mask attachment of FIG. 17.
Figure 18:
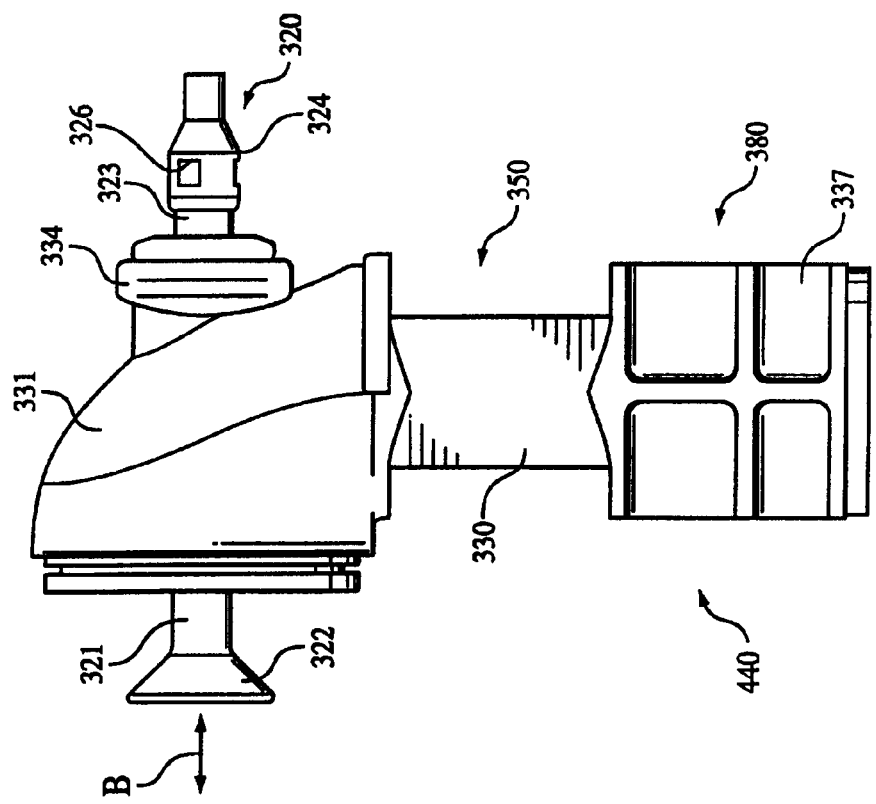
FIG. 18 is a side view of the mask attachment of FIG. 17.
Figure 20:
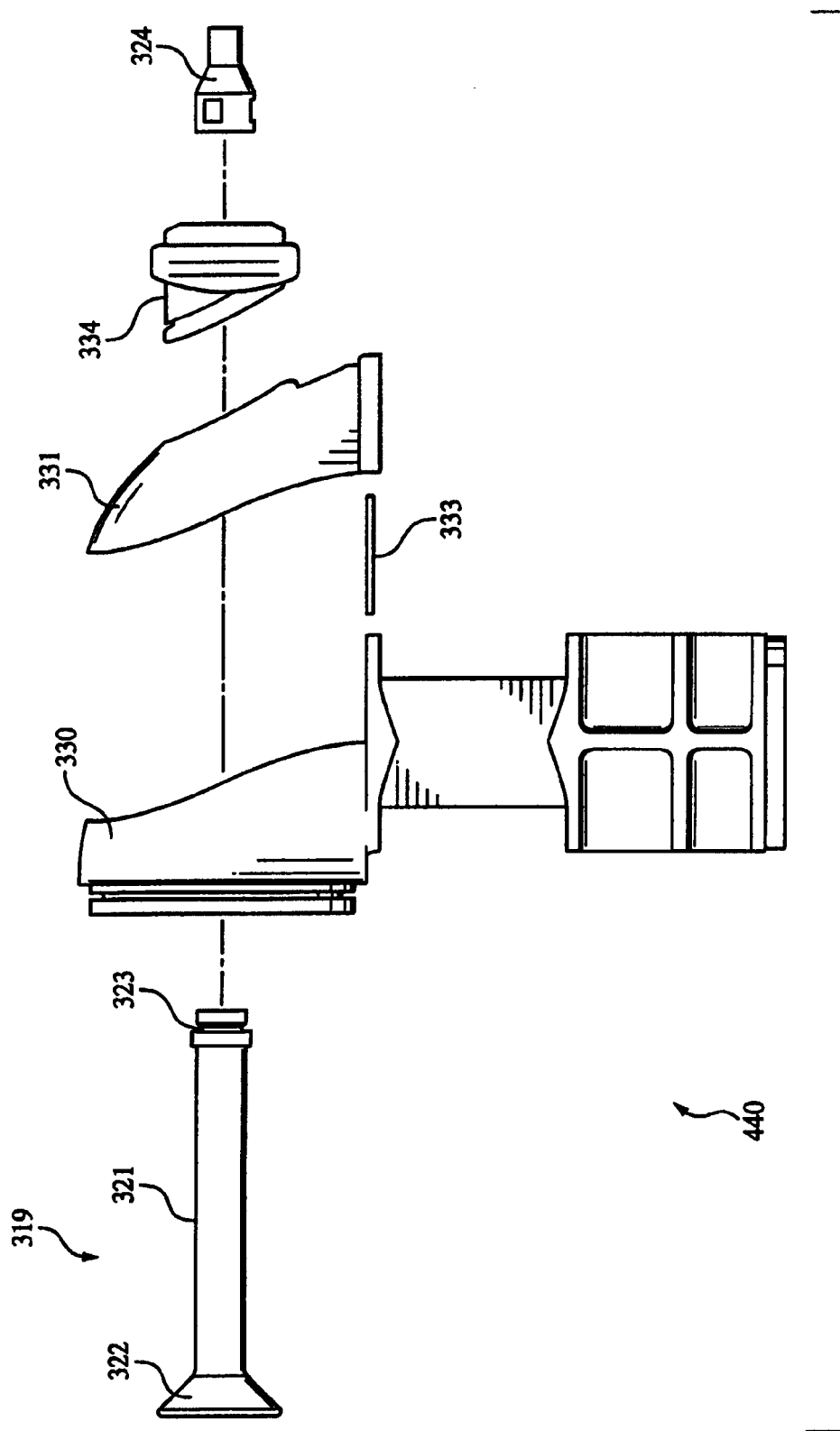
FIG. 20 is an exploded view the mask attachment of FIG. 17.

The embodiments of the patient interface assembly, including the mask and mask attachment, shown in FIGS. 1-14 are illustrative of only one possible assembly of these components. Other configurations for the mask and mask attachment are contemplated by the present invention. For example, the present invention contemplates that each of the sections of the mask attachment may be integrated with the mask, depending on the specifics of the manufacturing process chosen. FIGS. 15 and 16 illustrate a perspective and top view of a fifth embodiment of patient interface assembly 410 that includes a mask attachment 412 in which the mask connection section and an airway adapter section 416 are integrated into a mask shell 418. That is, the mask connection system is effectively eliminated, or is effectively combined with the airway adapter section, due to the direct coupling of the airway adapter section to the mask shell.

FIGS. 17-20 illustrates a sixth embodiment of a mask attachment 440 according to the principles of the present invention. Mask attachment 440 includes an entrainment valve and a gas collection adapter, both of which are discussed in detail below. In this embodiment, the mask attachment includes a mask connection section 320, an airway adapter section 350, and breathing system connection section 380. Mask attachment 440 includes a body member 330 and a cap 331 containing an opening attached to body member 330 via methods known in the art. In an exemplary embodiment, the body member and the cap are each single piece injection molded. They can also be separately molded, assembled with the other components and then joined. An end portion 337 of body member 330 is configured to comply with national or international standards. For example, the present invention contemplates that end portion 337 is a standard ISO fitting so that any device that complies with that standard can be coupled to the mask attachment. In the illustrated embodiment, end portion 337 includes multiple ribs.

A grommet 334 is inserted into an opening (not shown) defined in cap 331. A grommet cap 335 is provided to cover the opening in the cap by sealing over an opening in the grommet.

A flapper valve member 333, manufactured of a flexible material, such as rubber, serves as the entrainment valve and blocks the opening in cap 331 when the system is pressurized. The flapper valve functions as the entrainment valve in the same manner as the entrainment valve discussed above.

If it is desired to divert a sample of gas from within the mask to mask attachment 440, the mask attachment includes a gas collection adapter 319 positioned within the mask attachment. A tubing connector 324 is provided at one end gas collection adapter 319. Gas collection adapter 319, which may be made of rigid or flexible material, comprises a conical structure 322 with a central hole 325 to channel the flow of gas into a tubular portion 321 of the gas collection adapter. The length of tubular portion 321 of the gas collection adapter is selected so as to position conical structure 322 near the patient's oral cavity and nares to capture the user's expiratory gases. The present invention also contemplates that tubular portion 321 is movable relative to the mask attachment, as indicated by arrow B, to allow the end of the tube to be positioned near the user's nares. Friction between the tube and the grommet hold the tube in place. In addition to a conical structure, other structures for gas collection, such as prongs, are contemplated for use with the gas collection adapter. A flexible structure that may be positioned at or near the user's nares is also contemplated.

A ring or tabs (not shown) are provided on a distal end of tubular portion 321 to permit easy assembly of the tubular portion with tubing connector 324 by having the tabs mate with slots, tabs, a rim, or other mechanical fastener (not shown) in the tubing connector. An inner lumen of tubing connector 324 includes an internal grommet to permit easy connection to a conventional gas sampling tubing. Mating the outer surface of the gas sampling tubing to the inner lumen of the tubing connector minimizes the restriction of gas flow through the tubing connector and to the gas sampling tube (not shown) that connects to the tubing connector. Other means to connect the gas sampling tubing to the gas collection adapter, such as external barbs, are contemplated. Also, different tubing connectors with different features, and which the user can configure, are contemplated.

Similarly, the mask attachment may be combined with breathing circuit configurations known in the art, including but not limited to single limb or dual limb circuits. The mask attachment may be combined with valving known in the art, such as exhalation valves used in a single limb circuit. Other conventional components, such as humidifiers, bacterial filters, heaters, exhaust assemblies, pressure relief valves, flow sensor, temperature sensors, humidity sensors, and sampling ports can be provided in the mask, the mask attachment, or the breathing circuit.

Other respiratory gases, including trace respiratory gases, that are available endogenously, such as NO and CO, may be measured using a securably removable transducer or an integrated transducer provided on the airway adapter section of the mask attachment. Therapeutic gases such as NO, Oxygen, and Heliox (Helium and oxygen) may be measured. An $O_2$ mainstream sensor, when combined with the administration of oxygen as the therapeutic gas, may provide more accurate $O_2$ administration.

Additionally, the airway adapter section may be combined with, or optionally include, a flow measurement component. The flow measurement component may include pressure taps on each end of the airway adapter section that using a differential pressure measurement flow can be estimated. The pressure drop due to the cuvette although small would be sufficient to permit a reasonable estimate of flow to be made. For example, flow may be measured using pressure taps and differential pressure measurements as known in the art as well as optical methods using the apertures in the airway adapter section.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface assembly comprising:
   (a) a shell having a first shell opening and a second shell opening;
   (b) a seal comprising:
      (1) a first end portion coupled to the second shell opening, and
      (2) a second end portion adapted to contact a face of a patient; and
   (c) a mask attachment coupled to the first shell opening such that the mask attachment, the seal, and the shell define a unitary structure adapted to be assembled to a patient circuit and is fully supported on the mask, the mask attachment comprising:
      (1) a mask connection section having a first mask connection section end coupled to the first shell opening and a second mask connection section end,
      (2) an airway adapter section adapted for use in measuring a respiratory variable, wherein the airway adapter section includes a first airway adapter section end coupled to the second connection section end and a second adapter section end, and wherein the airway adapter section further comprises a gas measurement site comprising an infrared-transparent portion, a window including an infrared-transparent portion, or both, and
      (3) a breathing system connection section having a first breathing system connection section end coupled to the second airway adapter section end and a second breathing system connection section end adapted to be coupled to a patient circuit.

2. The patient interface assembly of claim 1, wherein the mask connection section is rotateably coupled to the shell.

3. The patient interface assembly of claim 1, further comprising an access port defined in shell, the mask connection section, or both.

4. The patient interface assembly of claim 3, wherein the access port is generally aligned with the first opening of the shell.

5. The patient interface assembly of claim 3, further comprising a cap adapted to selectively block the access port.

6. The patient interface assembly of claim 1, further comprising a transducer adapted to be coupled to the airway adapter section to measure such a respiratory variable.

7. The patient interface assembly of claim 1, wherein the airway adapter section is rotateably coupled to the breathing system connection section.

8. The patient interface assembly of claim 1, further comprising an entrainment valve disposed in the mask connection section.

9. A patient interface assembly comprising:
   (a) a shell having a first opening and a second opening;
   (b) a seal comprising:
      (1) a first end portion coupled to the second opening of the shell,
      (2) a second end portion adapted to contact a face of a patient; and
   (c) a conduit coupled to the shell; and
   (d) a gas measurement site disposed on the conduit, the shell, or both, wherein the gas measurement site is fully supported on the conduit or the shell or both, and wherein the gas measuring site includes:
      (1) an aperture defined in the conduit, the shell, or both,
      (2) a window covering the aperture, and
      (3) an infrared-transparent portion disposed in the window.

10. The patient interface assembly of claim 9, wherein the conduit is rotateably coupled to the shell.

11. The patient interface assembly of claim 9, further comprising an access port defined conduit, the shell, or both.

12. The patient interface assembly of claim 11, wherein the access port is generally aligned with the first opening of the shell.

13. The patient interface assembly of claim 9, further comprising a transducer adapted to be coupled to the gas measurement site to measure a respiratory variable.

* * * * *